United States Patent
Ramaekers

(10) Patent No.: US 8,357,663 B2
(45) Date of Patent: Jan. 22, 2013

(54) METHODS FOR ENHANCING FERTILITY COMPRISING ADMINISTRATION OF TRANSFER FACTOR

(75) Inventor: Joseph C. Ramaekers, Aptos, CA (US)

(73) Assignee: The Ramaekers Family Trust, Santa Cruz, CA (US)

( * ) Notice: Subject to any disclaimer, the term of this patent is extended or adjusted under 35 U.S.C. 154(b) by 0 days.

(21) Appl. No.: 12/325,199

(22) Filed: Nov. 30, 2008

(65) Prior Publication Data

US 2009/0170774 A1 Jul. 2, 2009

Related U.S. Application Data

(60) Provisional application No. 60/991,681, filed on Nov. 30, 2007.

(51) Int. Cl.
*A61K 35/00* (2006.01)
*A61K 35/54* (2006.01)
*A61K 35/20* (2006.01)
*A61K 35/14* (2006.01)

(52) U.S. Cl. ....... 514/21.3; 424/520; 424/561; 424/581; 424/529; 424/535; 530/300

(58) Field of Classification Search ................. None
See application file for complete search history.

(56) References Cited

U.S. PATENT DOCUMENTS

| | | |
|---|---|---|
| 4,220,666 A | 9/1980 | Fields |
| 4,237,118 A | 12/1980 | Howard |
| 4,435,384 A | 3/1984 | Warren |
| 4,761,402 A | 8/1988 | Williams et al. |
| 4,816,563 A | 3/1989 | Wilson et al. |
| 5,064,674 A | 11/1991 | Girsh |
| 5,080,895 A | 1/1992 | Tokoro |
| 5,185,166 A | 2/1993 | Nakagawa et al. |
| 5,190,775 A | 3/1993 | Klose |
| 5,211,956 A | 5/1993 | Sawai et al. |
| 5,234,698 A | 8/1993 | Fahim |
| 5,500,229 A | 3/1996 | Aalto et al. |
| 5,631,001 A | 5/1997 | Harich et al. |
| 5,753,696 A | 5/1998 | Shealy et al. |
| 5,759,543 A | 6/1998 | Morozova et al. |
| 5,833,948 A | 11/1998 | Tournier et al. |
| 5,840,700 A | 11/1998 | Kirkpatrick et al. |
| 5,883,224 A | 3/1999 | Kirkpatrick et al. |
| 5,993,221 A | 11/1999 | Bistrian |
| 6,013,286 A | 1/2000 | Klose |
| 6,156,320 A | 12/2000 | Izvekova et al. |
| 6,287,576 B1 | 9/2001 | Bgatov et al. |
| 6,468,534 B1 | 10/2002 | Hennen et al. |
| 6,506,413 B1 | 1/2003 | Ramaekers |
| 6,534,259 B1 | 3/2003 | Wakefield |
| 6,630,316 B1 | 10/2003 | Wier |
| 6,703,020 B1 | 3/2004 | Thorpe et al. |
| 6,939,864 B1 | 9/2005 | Johnson et al. |
| 6,962,718 B2 | 11/2005 | Ramaekers |
| 2002/0044942 A1 | 4/2002 | Dopson |
| 2002/0119928 A1 | 8/2002 | McAnalley |
| 2003/0077254 A1 | 4/2003 | Ramaekers |
| 2003/0129295 A1 | 7/2003 | Richardson |
| 2004/0241102 A1 | 12/2004 | Skelly |
| 2005/0255126 A1 | 11/2005 | Tsubaki et al. |
| 2006/0029585 A1 | 2/2006 | Ramaekers |
| 2006/0073197 A1 | 4/2006 | Ramaekers |
| 2007/0128253 A1 | 6/2007 | Ramaekers |
| 2009/0053197 A1 | 2/2009 | Ramaekers |
| 2009/0074751 A1 | 3/2009 | Ramaekers |

FOREIGN PATENT DOCUMENTS

| | | |
|---|---|---|
| CN | 1093267 A | 10/1994 |
| EP | 0366869 A | 5/1990 |
| JP | 02004024109 A | 1/2004 |
| WO | WO 92/00093 A | 1/1992 |
| WO | WO 96/26732 A1 | 9/1996 |
| WO | WO 97/11666 A | 4/1997 |
| WO | WO 02/087599 A1 | 11/2002 |
| WO | WO 2004/001053 A1 | 12/2003 |
| WO | WO 2005/112891 A2 | 12/2005 |

OTHER PUBLICATIONS

Sloan-Kettering on Dec. 19, 2009 (mskcc.org/mskcc/html/69399.cfm#References; 6 pages.*
Ginther, Animal Reproduction Science, 2000; 60-61: 61-79.*
Galli et al., Animal Reproduction Science, 2007; 98: 39-55.*
Akers, Michael J., Chapter 41 of Remington The Science and Practice of Pharmacy, 828 (David B. Troy ed., Lippincott Williams & Wilkins 2006), pp. 802-836.
Jenness, R. "The composition of human milk", Semin Perinatol., 1979, 3(3):225-39 (Abstract).
Harman, J., and Ward, M., The Role of Nutritional Therapy in the Treatment of Equine Cushing Syndrome and Laminitis, Alternative Medicine Review, 6(Supp), S4-S16, (2001).
Kahn, A et al., Transfer Factor in the Treatment of Herpes Simplex Types 1 and 2 Dermatologica, 163(2), 177-85 (1981).
McMeeking, A et al., A controlled trial of bovine dialyzable leukocyte extract for cryptosporidiosis in patients with AIDS, J. Infect. Disease, 161(1), 108-12 (1990).
Steele, RW et al., Transfer factor for the prevention of varicella-zoster infection in childhood leukemia, N. Engl. J. Med., Aug. 14, 303(7), 355-59 (1980).
Viza, D. et al., Use of specific transfer factor for the prevention or the treatment of herpes infections in mice and in man, J. Exp. Pathology, 3(4), 407-20.
Kirkpatrick, CH, Activities and characteristics of transfer factors, Biotherapy, 9:13-16, (1996).
Kirkpatrick, CH, Transfer factors: Identification of conserved sequences in transfer factor molecules, Molecular Medicine, 6(4):332-341 (2000).

* cited by examiner

*Primary Examiner* — Bridget E Bunner
*Assistant Examiner* — Christina Borgeest
(74) *Attorney, Agent, or Firm* — Fox Rothschild LLP

(57) ABSTRACT

Methods of promoting reproductive health in an animal by administering an effective amount of a composition containing at least one transfer factor are provided.

10 Claims, No Drawings

METHODS FOR ENHANCING FERTILITY COMPRISING ADMINISTRATION OF TRANSFER FACTOR

CROSS-REFERENCE TO RELATED APPLICATIONS

This application claims benefit under 35 U.S.C. §119(e) of U.S. Provisional Application No. 60/991,681, filed Nov. 30, 2007, the disclosure of which is hereby incorporated by reference herein, in its entirety.

FIELD OF THE INVENTION

This invention relates generally to the use of compositions and formulations comprising transfer factor in providing health benefits to animals. Such benefits include promoting reproductive health, including aspects of fertility and fecundity.

BACKGROUND OF THE INVENTION

The present invention relates to the use of compositions and formulations comprising transfer factor, particularly for promoting reproductive health in animals. Other U.S. patents and U.S. patent applications relate to the present invention, including without limitation, U.S. Pat. Nos. 6,506,413 and 6,962,718, U.S. Patent Provisional Application Nos. 60/573,113, 60/649,363, 60/701,860, and 60/814,777, U.S. patent application Ser. No. 11/762,727, U.S. Patent Application Publication Nos. 2006/0029585 A1, 2006/0073197 A1, and 2007/0128253 A1, all of which are incorporated herein by reference. Also related are PCT publications WO/2002/087599 and WO/2005/112891, incorporated herein by reference.

Transfer factors, which are produced by leucocytes and lymphocytes, are small water soluble polypeptides of about 44 amino acids that stimulate or transfer cell mediated immunity from one individual to another and across species but do not create an allergic response. Since transfer factors are smaller than antibodies, they do not transfer antibody mediated responses nor do they induce antibody production. The properties, characteristics and processes for obtaining transfer factor or transfer factors are discussed in U.S. Pat. Nos. 4,816,563; 5,080,895; 5,840,700, 5,883,224 and 6,468,534, the contents of which are hereby incorporated by reference into the present application.

Transfer factor has been described as an effective therapeutic for Herpes simplex virus (Viza, et al.), a treatment for acne blemishes, U.S. Pat. No. 4,435,384 and as a treatment against *C. albicans* (Khan et al.). Transfer factor has also been used to treat intestinal cryptosporidiosis in recipients treated with specific transfer factor (McMeeking, et al.). Still, et al. also showed that chicken pox infections were prevented by pretreatment of children treated with transfer factor from individuals that had chicken pox or who in other words had been sensitized to the varicella antigen. The antigen specific transfer factors are the most well studied and have been demonstrated to be able to convey the antigen recognition ability of the experienced donor to the naive recipient. It may be assumed that the individual or animal that is the source of the transfer factor has been sensitized to the antigen of interest. However, transfer factor as found in commercial bovine colostrum extract coming from a pool of animals (e.g., cows) contains the acquired immunity from all of the pool and therefore provides a type of generalized adoptive transfer of immunity. Transfer factors or transfer factor can be obtained from a dialyzable extract of the lyzed cells or from an extract of extracellular fluid containing transfer factor. Common sources of transfer factors are colostrums and ova. It is common practice to refer to preparations that contain transfer factor by the name of the active component (i.e., transfer factor or TF). Transfer factor extract containing transfer factors is also herein referred to as transfer factor. Transfer factor from bovine colostrum extract is defined as defatted water soluble material from colostrum that will pass through a nominal 10,000 molecular weight filter. The colostral derived transfer factor has been prepared with activity against various organisms including infectious bovine rhinotracheitis virus. One of the specific effects of transfer factor is a significantly increased natural killer (NK) cell activity. Natural killer cells provide protection against viruses as part of the innate immune defense system.

Although transfer factor is a polypeptide, it has been reported that it is surprisingly stable in the gastrointestinal tract. For example, Kirkpatrick compared oral versus parenteral administration of transfer factor in clinical studies. Kirkpatrick, *Biotherapy*, 9:13-16, 1996. He concluded that the results refute any arguments that the acidic or enzymatic environment of the gastrointestinal tract would prevent oral therapy using transfer factors.

When attempts were made to sequence TF, it was reported that an N-terminal end of the transfer factor peptide is resistant to sequential Edman degradation. Kirkpatrick, *Molecular Medicine*, 6(4):332-341 (2000).

Accordingly, transfer factor was believed to be stable in the gastrointestinal tract and rumen. However, it has since been shown that transfer factor is not as stable as once believed. It appears to be particularly unstable in the digestive tract of ruminants.

Transfer factors have been used successfully in compositions for treating animal diseases and syndromes including those in ruminants, as well as in other animals. See, for example, U.S. Pat. No. 6,962,718.

The present inventor has recognized an unmet need for effective compositions and methods for enhancing reproductive function in an animal.

BRIEF SUMMARY OF THE INVENTION

In certain aspects, the present invention is directed to methods of promoting reproductive health in an animal comprising the administration to a subject of an effective amount of a composition and/or formulation comprising at least one transfer factor.

Both the foregoing general description and the following detailed description are exemplary and explanatory, and are intended to provide further explanation of the invention as claimed. Other objects, advantages, and novel features will be readily apparent to those skilled in the art from the following detailed description of the invention.

DETAILED DESCRIPTION OF THE INVENTION

It has been found by the present inventor that the administration of compositions comprising transfer factor provides surprising and unexpected improvements in reproductive health and function. These results include, but are not limited to, improvements in fertility and fecundity in both males and females in a variety of animal species.

In certain embodiments, the present invention is directed to methods for enhancing the reproductive capability of an animal. In preferred embodiments, these methods comprise the administration to an animal of an effective amount of a composition and/or formulation comprising at least one transfer factor.

As used herein, the term "effective amount" refers to an amount of a compound, material, composition, formulation and/or dosage form as described herein that may be effective to achieve a particular biological result. Such results may include, but are not limited to, enhancement in the reproductive capability of an animal. An effective amount of a composition to enhance reproductive capability refers to an amount that causes an animal to demonstrate greater reproductive capability, including, but not limited to, fertility and/or fecundity, than an animal would otherwise demonstrate in the absence of the composition under otherwise prevailing conditions.

Transfer Factor

According to certain aspects of the invention, compositions and formulations are provided comprising transfer factor. According to certain embodiments of the invention, various forms of transfer factor may be used. They include, without limitation, excreted transfer factor released from transfer factor containing cells such as lymphocytes, leukocytes, and ova, and collected from extracellular fluids such as colostrums and blood. Another form includes preexcreted transfer factor found within the cell or on the cell surface. In certain embodiments of the invention, substantially purified transfer factor originating from leukocytes, colostrum, or ova and having a molecular weight of less than 10,000 daltons and a specific activity of at least 5000 units per absorbance unit at 214 nanometers, may also be used. The transfer factor used in the Examples of this invention and referred to in the following Tables and further referred to in the rest of the detailed description is generally extracted from colostrum collected from a general pool of lactating cows; although, in some cases, it is derived from eggs. Though bovine colostral derived transfer factor was generally used to develop the formulations of this invention, it is well known to anyone skilled in the art that other kinds and sources of transfer factor could be used.

Alternative sources of transfer factor include, but are not limited to, avian transfer factor, ova transfer factor, and transfer factor isolated from colostrum collected from non-bovine animals such as goats, pigs, horses and humans. In addition, combinations of transfer factors from any number of sources may be used in the formulations of the instant invention. Transfer factor may also be derived from recombinant cells that are genetically engineered to express one or more transfer factors or by clonal expansion of leukocytes.

Isolation of Transfer Factor

In certain embodiments of the invention, transfer factor may be obtained from colostrum. In a preferred embodiment, transfer factor is obtained from bovine colostrum. The fraction of colostrum comprising material having a molecular weight of approximately 10,000 daltons (Da) and below is designated as transfer factor. A fraction obtained that is approximately 10,000 to approximately 150,000 Da is designated an antibody fraction, also known as an antibody-colostrum fraction. In certain embodiments, a colostral fraction having a molecular weight of about 10,000 to about 400,000 Da may be used as an antibody fraction. The fraction comprising material having a molecular weight of approximately 10,000 Da and above is designated as the growth factor fraction. The growth factor fraction may include high molecular weight proteins.

In certain embodiments, an antibody fraction comprises antibodies from about 1% to about 99%, about 5% to about 95%, about 10% to about 90%, about 15% to about 85%, about 20% to about 80%, about 25% to about 75%, about 30% to about 70%, about 35% to about 65%, about 40% to about 60%, about 45% to about 55%, or about 50% by weight, the remainder comprising other colostrum components.

According to certain embodiments of the invention, transfer factor, as used in the formulations described in the Tables, particularly when not defined as obtained from an avian source, may be further defined as defatted water soluble material from bovine colostrum that will pass through a nominal 10,000 molecular weight filter.

In other embodiments, the transfer factor may be obtained from an avian source. In one embodiment, chickens are given a feed mixture containing excrement from an animal, including without limitation, at least one selected from the group consisting of a human, a fish, a goat, a llama, an alpaca, a pig, a sheep, a cow, and a horse. The excrement will contain a large variety of pathogens and upon administration in a feed to an animal, the animal will develop transfer factor and/or antibodies to such pathogens. Avian transfer factor can then be obtained from the eggs produced by the above-treated chickens. In certain embodiments of the invention, transfer factor may be found in whole egg yolks. As a non-limiting example, the transfer factor of avian source (which is believed to also contain antibodies) listed in the formulation of Table 3 is supplied as powdered whole egg yolks.

Alternative kinds of transfer factor include, but are not limited to, targeted transfer factors. Target transfer factors include transfer factor collected from sources which have been exposed to (1) one or more viral or otherwise infectious organisms; (2) one or more antigens that produce an immune response; or (3) a combination of organisms and antigens. The term antigen is defined herein is anything that will initiate the cell mediated immune response. Examples of such viral or other infectious organisms include Herpes Simplex Virus 1, Herpes Simplex Virus 2, H. Pylori, *Camphobacter and Chlamydia*, Bovine Rhinotracheitis Virus, Parainfluenza, Respiratory Syncytial Virus Vaccine, modified live virus, *Campylobacter Fetus, Leptospira Canicola, Grippotyphosa, Hardjo, Leterohaemorrhagiae, Pomona Bacterin, Bovine Rota*-Coronavirus, *Escherichia Coli* Bacterin, *Clostridium Chauvoei, Septicum, Haemolyticum, Novy, Sordellii*, Perfringens Types C & D, Bacterin, Toxoid, Haemophilus Somnus, Pasteurella Haemolytica, Multocida Bacterin. However, one of skill in the art would readily recognize that a wide variety of other viral and otherwise infectious organisms can find use in the instant invention.

Additionally, transfer factor and antibodies may be derived from any suitable source, as described, for example, in U.S. Pat. Nos. 4,816,563; 5,080,895; 5,840,700; 5,883,224; and 6,468,534; and U.S. patent application Ser. No. 11/762,727, the contents of which are hereby incorporated by reference herein.

In certain embodiments, the component of a given formulation that is referred to as the "transfer factor" may optionally include a colostral component of higher molecular weight; for example, a portion of the fraction referred to above as an antibody or antibody-colostrum fraction. In certain embodiments, the mammalian "transfer factor" component of a formulation comprises both transfer factor fraction and antibody fraction. In certain preferred embodiments, "mammalian transfer factor" comprises about 70% transfer factor fraction from colostrum (i.e., 10,000 Da or below colostrum fraction) and about 30% antibody colostrum fraction. In other preferred embodiments, "mammalian transfer factor" comprises about 80% transfer factor fraction from colostrum and about 20% antibody colostrum fraction. (The foregoing are in weight percents of the composition). In certain embodiments, the "transfer factor" component of the composition or formulation may include one or both of mammalian and avian transfer factor.

Lyophilization

The present invention also provides compositions and formulations that have one or more lyophilized component(s). Lyophilization or "freeze-drying" is a process well known to those of ordinary skill in the art. For example, some techniques of lyophilization are described in Akers, Michael J., Chapter 41 in Remington The Science and Practice of Pharmacy, 828 (David B. Troy ed., Lippincott Williams & Wilkins 2006), which is incorporated herein by reference. In certain embodiments, formulations and/or compositions of the present invention may include lyophilized transfer factor. In certain embodiments, transfer factor, which may be lyophilized, may be combined with one or more of: an antibody or an antibody fraction, a growth factor fraction, or some other colostral fraction; one or more of which may, in certain embodiments, be lyophilized. In other embodiments, additional components of formulations and compositions of the invention may be lyophilized, including, without limitation, other peptides and proteins.

Formulations

In certain embodiments of the invention, transfer factor is provided in a formulation that further comprises one or more additional ingredients. In preferred embodiments, the formulation comprises transfer factor and at least one glucan. In some embodiments, transfer factor fraction and at least one glucan is provided in a formulation that further comprises one or more additional ingredients. In certain embodiments, the transfer factor fraction may be lyophilized. In certain embodiments, the optional antibody or antibody fraction may be lyophilized.

In a preferred embodiment, transfer factor is present in the formulation in the amount of about 10 mg to about 12 gm/oz, more preferably about 100 mg to about 6 gm/oz and most preferably about 10 mg to about 3 gm/oz. In certain preferred embodiments, such a formulation comprising transfer factor is provided to an animal in an amount of about 1 oz per 1000 lb of animal.

In certain embodiments of the invention, formulations are provided which comprise glucans. Glucans may be derived from any suitable source, including, but not limited to, fungi, oats, and yeast. Preferably, glucans are present in or derived from fungi. In certain embodiments, the glucans which may be included in the formulations are present in whole fungi. In certain preferred embodiments, glucans are present in or derived from *Cordyceps*, more preferably, *Cordyceps sinensis*.

In certain embodiments, glucans are derived from hybrid strains of fungi. In a preferred embodiment the hybrid glucans used in the invention are present in, or derived from, hybrid strains of *Cordyceps* and in particular *Cordyceps sinensis*. One technique to induce the hybridization of *Cordyceps* involves plating two different strains or species on a single agar plate which has been inoculated with rattlesnake venom as described in, for example, U.S. Patent Application Publication No. 2006/0073197, published Apr. 6, 2006, and U.S. Patent Application Publication No. 2007/0128253, published Jun. 7, 2007, each of which is incorporated herein by reference. In a preferred embodiment, the hybrid strain producing the hybrid glucans that may be used in compositions and formulations of the invention is *Cordyceps sinensis* Alohaensis, which is available from Pacific Myco Products, Santa Cruz, Calif.

In addition to *Cordycep sinensis* hybrids, suitable sources of glucans may include, but are not limited to, *Agaricus blazeii, Coriolus, Poira Cocos, Inonotus obliquus*, Maitake Mushroom, Shiitake Mushroom, and combinations thereof.

When glucans are used, the formulation preferably contains about 10 mg to about 18 gm of whole organism/oz, more preferably about 100 mg to about 10 gm of whole organism/oz and most preferably about 100 mg to about 5 gm of whole organism/oz.

Equivalent amounts of purified or partially purified glucan as well as the nucleosides associated therewith (e.g., Cordycepin (3'deoxyadenosine), adenosine and N6-(2 hydroxyethyl)-adenosine) may also be used.

In certain preferred embodiments of the invention, formulations that may be administered to a subject, may comprise, in addition to transfer factor, which, in preferred form, may be derived from mammalian and/or avian source, one or more of the following: at least one glucan, mammalian antibody-colostrum fraction, mammalian growth factor fraction, other mammalian colostral fraction, and avian antibodies or antibody fraction (which may, in certain embodiments, be obtained from whole egg yolk).

In certain preferred embodiments, compositions may further comprise one or more of inositol hexaphosphate (Ip6), mannans, olive leaf extract, and phytosterols. In certain preferred embodiments, mannans are derived from Aloe vera. In certain preferred embodiments, phytosterols may be derived from soya bean.

In certain embodiments, compositions may further comprise one or more of lactic acid producing bacteria, ascorbic acid, Vitamin A, Vitamin D3, Vitamin E, Vitamin B1, Vitamin B2, Vitamin B12, dipotassium phosphate, potassium chloride, magnesium sulfate, and calcium pantothenate.

In certain embodiments, compositions and formulations comprising transfer factor may be combined with minerals, antioxidants, amino acids, and other nutraceuticals.

In certain embodiments, the invention provides compositions and formulations in which one or more components are encapsulated. Encapsulation may be achieved by mixing the component to be encapsulated with a hydrophobic substance or a lipid to form a coating around the component. Encapsulation may protect labile components from inactivation in the gastrointestinal tract. Such encapsulation may be important especially in the case of ruminants where digestion within the rumen has been found to interfere with the administration of certain labile factors. Enhanced bioavailability has been demonstrated, for example, when a transfer factor is encapsulated and administered to ruminants.

Previous use of non-encapsulated transfer factor in ruminants, e.g., cows, produced significant beneficial results. See, e.g. U.S. Patent Publication 2003/0077254, published Apr. 24, 2003 incorporated herein by reference in its entirety. Subsequently, it was discovered that transfer factor was not stable by oral administration in a stressed population of cattle. After discovering that transfer factor is inactivated in vitro in the presence of rumen fluid and flora, it was determined that prior success with transfer factor in ruminants was due to the presence of the esophageal groove. When not stressed, the esophageal groove provides partial bypass of the rumen. However, in a stressed population the esophageal groove closes and shunts the transfer factor formulation into the rumen. It was discovered that encapsulating transfer factor and/or glucans with a hydrophobic substance or a lipid to form an encapsulated formulation is sufficient to provide substantial by-pass of (e.g., about 85%) of the rumen even in a stressed population.

While not intending to be bound by any theory or theories of operation, it is believed that encapsulation of transfer factor fraction may increase its bioavailability upon administration to fermenting animals, such as adult ruminants.

In preferred embodiments, the transfer factor is encapsulated by mixing with a hydrophobic substance or a lipid to form a coating around the growth factor(s). In additional embodiments, one or more additional components such as antibody, antibody fraction, and/or glucans may be encapsulated. Other optional components of compositions and formulations of the invention may be encapsulated, such as, without limitation, inositol hexaphosphate, olive leaf extract, mannans, phytosterol, vitamin C and mixtures thereof. The transfer factor, antibody or antibody fraction and/or additional optional components may each be individually encapsulated or encapsulated as a mixture. Alternatively, the entire formulation can be encapsulated. The encapsulated component(s) and/or formulation can be produced in a variety of ways. In a preferred embodiment, each of the transfer factor, glucans, antibody or antibody fraction and/or additional labile component(s) in the formulation may be encapsulated as described in U.S. Pat. Nos. 5,190,775, 6,013,286 and U.S. Application 2003/0129295, each of which is incorporated herein by reference in its entirety.

The transfer factor may be encapsulated with a hydrophobic or lipid coating that is preferably between about 25% and about 150 wt % of the transfer factor, about 50-150 wt % and about 75-125 wt %, with an equal weight being most preferred.

In additional embodiments of the invention, additional components may be used in the formulation administered. Particular components may be encapsulated. For example, IP6, β-sitosterol, olive leaf extract, aloe extract matter and/or vitamin C may be used; in certain embodiments, one or more of these components may be encapsulated. In preferred embodiments, IP6 is present at between 10 mg and 3 gm/oz, or one preferably between 100 mg and 2 gm/oz, and most preferably between 100 mg and 1 gm/oz. The β-sitosterol is preferable in the amount of between 10 mg and 3 gm/oz, or preferably between 100 mg and 2 gm/oz, and most preferably between 100 mg and 1 gm/oz. Olive leaf extract is preferably present in the amount of 2 mg to 2 gm/oz, more preferably between 5 mg and 1 gm/oz, and most preferably between 5 mg and 500 gm/oz. Aloe extract is preferably present at between 2 mg and 1000 mg, more preferably between 5 and 500 mg/oz, and most preferably between 5 and 250 mg/oz. Vitamin C may be present at between 10 mg/oz and 10 gm/oz, or preferably between 100 mg and 8 gm/oz, and most preferably between 100 mg and 5 gm/oz.

In certain embodiments, glucans of the formulation may be encapsulated, preferably with a hydrophobic or lipid coating. It is preferred that the amount of hydrophobic or lipid coating be between about 25% and 150 wt % of the glucan, about 50-150 wt %, or about 75-125 wt %, with an equal weight being most preferred.

Columns 2, 3 and 4 of Tables 1-3 show the approximate high, low and preferred amounts, respectively, of the formulation components, in amounts per body weight, to be given to an animal in a single dosage. The formulation represented in Table 2 is designed preferably for livestock. The 5 ounces of the formula listed in column 5 is designed to be given to a 1000 pound animal but that will vary and could be given to a 500 pound animal in some cases. The average horse is around 1000 pounds. However, since these formulas are comprised of nutraceuticals and transfer factor, one skilled in the art will recognize that the ranges are not certain and as critical as the ranges for allopathic drugs.

Table 3 provides an exemplary encapsulated transfer factor formulation for administration to subjects. In certain embodiments, a transfer factor formulation includes at least encapsulated transfer factor derived from bovine and/or avian sources, and/or one or more of hybrid glucans. It is preferred that the glucan portion of this formulation also be encapsulated. Other components include zinc proteinate, targeted avian transfer factors, β-sitosterol, inositol hexaphosphate (IP6), olive leaf extract, aloe extract powder, probiotics, *B. subtlis, B. longum, B. thermophilium, L. acidophilus, E. faecium*, and *S. cerevisiae*. In a preferred embodiment, all of the foregoing are included in this transfer factor formulation.

In another preferred embodiment, a formulation is provided according to Table 3, but with the following modifications. The component listed as "Transfer factor (mammal source)" is substituted with a composition containing 80% bovine colostrum transfer factor as described herein, combined with 20% bovine colostrum antibody fraction as described herein (both weight percents of the composition). In certain embodiments, the mammalian transfer factor and the colostrum antibody fraction are both lyophilized. In a preferred embodiment, the component listed as "Transfer factor (avian source)" is present in the formulation in an amount of 3000.0 mg/oz. This component may be supplied as powdered whole egg yolk obtained from hyperimmunized chickens, i.e., chickens that had been exposed to pathogens prior to laying the eggs which serve as a source of transfer factor. In various embodiments, the avian transfer factor may be obtained from commercial sources such as, for example, 4LIFE® Research; Labelle, Inc., Bellingham, Wash.; Troue; and Ghen Corporation, Japan.

The amount of transfer factor and/or antibody or antibody fraction used in the formulation or the amount of formulation administered will vary depending upon the severity of the clinical manifestations presented. In addition, the amount of transfer factor administered to a recipient will vary depending upon the species from the transfer factor is derived as compared to the species of the recipient. It has been observed that transfer factor derived from bovine species administered to cattle is more efficacious than transfer factor from another species such as avian species. Accordingly, when the source of the transfer factor and recipient are different species, it is preferred that the amount of transfer factor be increased.

It is preferred in formulations used in the methods described herein that the metal nutraceuticals are proteinated because these forms are easier for the animal to digest and also because the proteinate forms are more stable to pH. The nutraceutical components in the formulations in Tables 1-3 are active components for treating the various described conditions. The fillers and carriers are included to make the formulations more palatable to the animal and also to help preserve the mixture. These include silicon dioxide, maltodextrin, soy and peanut flour, peanut oil, dextrose, whey, spices and flavorings. Mixed tocopherols and choline chloride are nutraceuticals but the effective results described herein can still be achieved by deleting these two components from the formulations.

Methods of Administration

As discussed herein, it was discovered that encapsulating transfer factor and/or glucans with a hydrophobic substance or a lipid to form an encapsulated formulation is sufficient to provide substantial by-pass of (e.g., about 85%) of the rumen even in a stressed population of ruminants.

A variety of other methods for rumen by-pass are known. In one embodiment, the encapsulated or non-encapsulated formulation is directly injected (subcutaneously, intramuscularly, or intravenously) to by-pass not only the rumen but also the entire digestive system. Similarly, intravaginal, intrarectal or other direct administration to mucus membranes, such as the eye subconjunctival, by-pass the digestive system and the rumen in particular. Alternatively, the formulation can be mixed with various solvents which allow for direct skin absorption. Furthermore, methods are known in the art to stimulate opening of the esophageal groove in various ruminants and such opening allows for immediate passage of an orally administered formulation to the gastrointestinal tract, by-passing the rumen.

In certain embodiments, transfer factor compositions and/or formulations may be included in food. Preferred embodiments for human consumption include, but are not limited to incorporation of transfer factor formulations in processed foods such as cereals, snacks, chips, or bars. Preferred embodiments for animal consumption include, but are not limited to, transfer factor formulations admixed in feed pellets, salt licks, molasses licks or other processed feed products.

Other methods of administration to animals, including, but not limited to, drenching, may also be employed.

The transfer factor formulations used in the present invention include pharmaceutical compositions suitable for administration. In a preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as sodium acetate; fillers such as microcrystalline cellulose, lactose, corn and other starches; binding agents; sweeteners and other flavoring agents; coloring agents; and polyethylene glycol. Additives are well known in the art, and are used in a variety of formulations.

In a further embodiment, the pharmaceutical compositions may be added in a micellular formulation; see U.S. Pat. No. 5,833,948, hereby expressly incorporated by reference in its entirety.

In certain aspects, the components of the compositions and pharmaceutical formulations of the present invention may have an effect upon administration individually, such as, for example, the enhancement of aspects of reproductive function, but upon administration in one or more combinations, have an effect that is synergistic. By "synergistic" is meant an enhancement of the effect of one or more combined components in a more than additive fashion relative to the effect of each component when used alone.

In certain embodiments, the present invention provides methods involving administration of compositions and/or formulations comprising transfer factor to a subject. As used herein, the term "subject" is used to mean an animal, including, without limitation, an avian or a mammal. Mammalian subjects include, without limitation, primates, bovines, porcines, ovines, equines, caprines, and carnivores, including, but not limited to, felines and canines. The mammal may be a human.

Combinations of pharmaceutical compositions may be administered. Moreover, the compositions may be administered in combination with other therapeutics.

In certain embodiments, the present invention provides methods of treating a subject by administering a composition or formulation comprising transfer factor, as described herein. In certain embodiments, such methods are provided for improving the reproductive health of the subject by administration of transfer factor. In particular embodiments, methods are provided of increasing fertility and/or fecundity in a subject by the administration of transfer factor. As used herein, "fertility" refers to the ability to produce offspring. As used herein, "fecundity" refers to the efficiency of an individual in production of young. Animals that bring forth young frequently, regularly, and, in case of those that bear more than one offspring at a birth, in large numbers, are said to be fecund.

In certain embodiments of the invention, the subject is female. In other embodiments, the subject is male.

In certain aspects, methods according to the invention may be used to improve the rate of conception in female subjects. Example 6 demonstrates the positive effects of the administration of a transfer factor formulation on the rate of conception in sheep. Example 8 demonstrates the positive effects of the administration of a transfer factor formulation on the rate of conception in pigs.

In certain aspects, administration of transfer factor to subject may be used to increase the number of offspring born alive to the subject.

In certain aspects, methods according to the invention may be used to improve the quality and/or quantity of ova and/or zygotes that may be obtained from female donor animals. Embryos from donor animals are subsequently transferred into recipient females, which give birth to the offspring.

In a particular embodiment, transfer factor is administered to a donor animal that is a cow. Examples 1 and 3 demonstrate the positive effects of administration of transfer factor formulation on the quantity and quality of eggs produced by donor cows.

In other embodiments, male reproductive health and function may be improved by the administration of compositions and/or formulations comprising transfer factor. This function may include improvements in the quantity and/or quality of sperm produced by the male. Example 5 demonstrates the positive effect of administration of transfer factor on the viability of sperm produced by the animal. Such effects may increase the commercial value of animals whose sperm is a commodity.

Other examples demonstrate efficacy of transfer factor formulations in improving reproductive health and function. Example 10 describes the return to reproductive health of a mare diagnosed with an ovarian tumor after a course of treatment involving administration of a transfer factor formulation. In certain embodiments, administration of transfer factor according to the methods described herein may cause an improvement in the endocrine function of the subject.

Without intending to be bound by any theory or theories of operation, it is postulated that at least some of the beneficial effects of transfer factor on reproductive health may be due to the reduction of (possibly undiagnosed) tumors or cysts in the reproductive organs that may compromise reproductive function in the animal.

Additional benefits of transfer factor on reproductive health and function may be obtained. Without intending to be bound by any theory or theories of operation, the following benefits may be obtained by the administration of transfer factor to a subject. Administration of transfer factor may improve the balance of cortisol in the subject, thereby reducing the effects of stress, which, in turn, may lead to good endocrine function prior to breeding and/or conception. Administration of transfer factor is thought to lead to improved immune health, thus providing a female subject with a "clean" oviduct and/or endometrium (lining of the uterus), thus providing a fertile bed for implantation of fertilized eggs. Regarding the improvement in egg quality that has been described herein, it is possible that the health benefits of transfer factor may include the induction of a cascade of good endocrine function, leading to luteal activity that produces high-quality ova (eggs).

EXAMPLES

The following examples serve to more fully describe the manner of using the above described invention. It is understood that these examples in no way serve to limit the true scope of this invention, but rather are presented for illustrative purposes.

TABLE 1

Transfer Factor Formula (No Encapsulation)
(Amounts in mg/lb of body weight unless otherwise stated)

| Component | Dosage: mg/oz. (unless otherwise noted) of formula |
|---|---|
| Transfer factor (mammal source) | 1750.0 |
| Transfer factor (avian source) | 750.0 |
| β-sitosterol (90% phytosterols) | 150.0 |
| Inositol hexaphosphate | 175.0 |
| Olive leaf extracts | 17.5 |
| *Aloe* extract powder (200:1) | 8.5 |
| Hybridized and non-hybridized Glucans (from Hybridized *Cordyceps sinensis*, *Agaricus blazeii*, *Miatake*, *Shitake*, *Coriolis*, *Inonotus obliquus*, and *Poris cocos* mushrooms) | 2000.0 |
| Vitamin C | 1000.0 |
| Vitamin A | 4434 IU/oz |
| Vitamin D3 | 1140 IU/oz |
| Vitamin E | 500 IU/oz |
| Vitamin B1 | 12.77 |
| Vitamin B2 | 12.77 |
| Vitamin B12 | 1.5 |
| Di-potassium phosphate | 1.5 g/oz |
| Potassium chloride | 207 |
| Magnesium sulfate | 83 |
| Calcium pantothenate | 23 |
| Ascorbic acid | 23 |
| Lactic acid bacteria | $2.5 \times 10^6$ CFU/oz |
| Yeast (*S. cerevisiae*) | $15.0 \times 10^6$ CFU/oz |
| Zinc proteinate | 10 |

*These amounts are calculated for livestock animals weighing about 450 to 1,000 pounds, goats weighing about 150 pounds, and dogs and cats weighing from about 8 to about 15 pounds.

TABLE 2

(Amounts in mg/lb of body weight unless otherwise stated)

| Component | High | Low | Preferred | Dosage: mg/5 oz. of formula |
|---|---|---|---|---|
| 1-Arginine | 0.5 | 0.005 | 0.05 | 50.00 |
| *Lacto yeast (4.9% of blend) | 69.51 | 0.6951 | 6.91 | 6951.88 |
| Montmorillinite | 1 gm/lb | 0.24118 | 2.4118 | 2411.88 |
| Soybean oil (14.5% mix) | 1.5 gm/lb | 2.05 | 20.571 | 20571.88 |
| Safflower oil (14.5% mix) | 1.5 gm/lb | 2.05 | 20.57 | 20571.88 |
| Flax seed oil (55% Alpha Linolenic Acid) (1.0% mix) | 1.5 gm/lb | 2.05 | 20.571 | 1418.75 |
| Phosphorous (Monosodium phosphate) 12% | 15.750 gm | 0.0525 | 5.08 | 5080.00 |
| Calcium carbonate 8.5% (38% calcium) | 13.68 gm | 0.0485 | 4.88 | 4880.00 |
| Methyl sulfonyl methane | 20 | 0.02 | 2 | 2000.00 |
| Vitamin C (ascorbic acid) | 21.62 | 0.2162 | 2.162 | 2162.50 |
| d-Biotin (Vitamin H 2%) | 9.73 | 0.000973 | 0.00973 | 10.00 |
| Vitamin D3 | 29.16 IU | 0.7298 IU | 7.298 IU | 7298.38 IU |
| Vitamin B12 | 0.092 | 0.000092 | 0.00092 | 0.92 |
| Folic Acid | 1 | 0.001006 | 0.01006 | 10.06 |
| Niacinimide | 12 | 0.012157 | 0.12157 | 121.57 |
| Pantothenic acid (d-Calcium Pantothenate) 91.6% | 0.324 | 0.0108 | 0.108 | 108.00 |
| Vitamin B6 (Pyridine Hcl) 82.3% | 1.158 | 0.001158 | 0.01158 | 11.58 |
| Vitamin A (Retinol Palmitate) 650M IU/g feed grade | 600 IU | 4.02 IU | 40.212 IU | 40232.50 IU |
| Vitamin B2 | 0.0554 | 0.002776 | 0.02776 | 27.76 |
| Thiamine (Mononitrate) 83% | 3.09 | 0.00308 | 0.0308 | 30.80 |

TABLE 2-continued (Amounts in mg/lb of body weight unless otherwise stated)

| Component | High | Low | Preferred | Dosage: mg/5 oz. of formula |
|---|---|---|---|---|
| Vitamin E | 72.9 IU | 0.0729 IU | 0.729 IU | 729.42 IU |
| Vitamin K | 1 | 0.0007 | 0.007 | 7.00 |
| Cobalt (Proteinate) 5% | 0.00043 | 0.000043 | 0.00043 | 0.43 |
| Copper (Proteinate) 10% | 0.56 | 0.0112 | 0.112 | 112.00 |
| Iodine (Potassiumiodide) 98% | 0.005 | 0.000053 | 0.00053 | 0.53 |
| Iron (Proteinate) 15% | 3.31 | 0.0331 | 0.331 | 331.16 |
| Magnesium (Oxide) 58% | 10 | 0.04 | 0.4 | 400.00 |
| Manganese (Proeinate) 15% | 1.65 | 0.04 | 0.4 | 332.10 |
| Molybdenum (Sodium Molybdate Dihydrate) 39% | 0.05 | 0.001 | 0.01 | 10.00 |
| Selenium (Sodium Selenite) 44.8% | 0.00162 | 0.000081 | 0.00081 | 1.00 |
| Zinc (Proteinate) 15% | 50 | 0.04987 | 0.4987 | 498.72 |
| 1-Lysine (Mono HCl) | 8.41 | 0.0841 | 0.841 | 841.57 |
| d,1-Methionine | 11.03 | 0.1103 | 1.103 | 1103.86 |
| Mixed Tocopherols | | | | 300.00 |
| Choline Chloride | | | | 2434.00 |
| Sipernat 50 (Silicon dioxide) | | | | 12768.75 |
| Lodex-5 (maltodextrin) | | | | 7519.38 |
| Soy flour (17.5% mix) | | | | 24828.13 |
| Sweet whey | | | | 996.00 |
| BF70 spice | | | | 146.00 |
| Dextrose powder | | | | 750.00 |
| Transfer factor - blend of 70% mammalian and 30% avian | | | | 750.00 mg/ 141 gram |
| Olive leaf extract, Ip6, mannins and phytosterol blend | | | | 750.00 mg/ 141 gram |
| Poly R blend of Glucans (from Hybridized *Cordyceps sinensis*, *Agaricus blazeii*, *Miatake*, *Shitake*, *Coriolis*, *Inonotus obliquus*, and *Poira cocos* mushrooms) | | | | 1000 mg/141 grams |

*Lactic acid generating bacteria is two-thirds of component and yeast is one-third; lactic acid generating bacteria is 500,000,000 CFU/gm, yeast (e.g., "*Saccharamyces*") 250,000,000 CFU/gm

TABLE 3

Livestock Stress Rumen By-Pass
(Amounts in mg/lb of body weight unless otherwise stated)

| Component | Dosage: mg/oz. (unless otherwise noted) of formula |
|---|---|
| Stabilized[1] | |
| Transfer factor (mammal source) | 3500.0 |
| Transfer factor (avian source) | 1500.0 |
| β-sitosterol (90% phytosterols) | 300.0 |
| Inositol hexaphosphate | 350.0 |
| Olive leaf extracts | 35.0 |
| *Aloe* extract powder (200:1) | 17.0 |
| Hybridized and non-hybridized Glucans (from Hybridized *Cordyceps sinensis*, *Agaricus blazeii*, *Miatake*, *Shitake*, *Coriolis*, *Inonotus*, *Obliquus*, and *Poris cocos* mushrooms) | 4000.0 |
| Vitamin C | 2000.0 |
| Non-Stabilized | |
| Vitamin A | 4434 IU/oz |
| Vitamin D3 | 1140 IU/oz |
| Vitamin E | 500 IU/oz |
| Vitamin B1 | 12.77 |
| Vitamin B2 | 12.77 |
| Vitamin B12 | 1.5 |
| Di-potassium phosphate | 1.5 g/oz |
| Potassium chloride | 207 |
| Magnesium sulfate | 83 |
| Calcium pantothenate | 23 |
| Ascorbic acid | 23 |
| Lactic acid bacteria | $2.5 \times 10^6$ CFU/oz |
| Yeast (*S. cerevisiae*) | $15.0 \times 10^6$ CFU/oz |
| Zinc proteinate | 10 |

*These amounts are calculated for livestock animals weighing about 450 to 1,000 pounds, goats weighing about 150 pounds, and dogs and cats weighing from about 8 to about 15 pounds.
[1]Stabilized active ingredients are included in a formulation of 50% soybean oil and 50% active ingredient.

Example 1

Effects of Transfer Factor on Yields of Bovine Embryos

The effects of formulations containing transfer factor was investigated in cows intended to be used as donors for embryo transfer. In this process, fertilized ova are flushed from the uterus of a donor cow and subsequently implanted in a recipient cow. Individual fertilized eggs (referred to herein as "embryos"; also termed "zygotes") are examined via microscope and evaluated for quality; each embryo being classified numerically as to the potential likelihood of success if transferred to a recipient cow. The major criteria for evaluation include: regularity of the shape of the embryo; compactness of the blastomeres (the dividing cells within the boundaries of the embryo); variation in cell size; color and texture of the cytoplasm; overall diameter of the embryo; presence of extruded cells; regularity of the zona pellucida; and the presence of vesicles. Using these subjective criteria, embryos are classified as: Grade 1: Excellent or Good; Grade 2: Fair; Grade 3: Poor; Grade 4: Dead or degenerating. (See, e.g., Embryo Transfer in Cattle, Glenn Selk, Oklahoma State University, No. 3158). Higher grade embryos are also more likely to survive storage by freezing. Overall, a Grade 1 egg has about a 98% probability of leading to conception in recipient cows, while lower grades have about a 60% or lower chance of implanting in the uterus and thus are much less likely to produce a pregnancy in a recipient.

Nine cows were given 1 oz of the formulation described above in Table 3 on Day 7 and Day 6 prior to the removal of embryos from the donor via flushing. The following table shows the total number of eggs recovered from a given donor animal and the number of eggs graded as number 1 (highest quality embryos), as documented before transfer factor (TF) formulation was supplied, and the increases in both quantity and quality of embryos recovered after administration of formulation comprising transfer factor.

TABLE 4

| | Flush Results - No TF | | Flush Results Post-TF | |
|---|---|---|---|---|
| Animal | Total Number of Embryos | Number of Grade 1 Embryos | Total Number of Embryos | Number of Grade 1 Embryos |
| 1 | 9-16 | 6 | 27 | 27 |
| 2 | 6-12 | 4 | 27 (1 #2 embryo) | 26 |
| 3 | 2-6 | 4 | 12 | 12 |
| 4 | 3-9 | 6 | 16 | 16 |
| 5 | 4-7 | 4 | 16 | 16 |
| 6 | 2-6 | 3 | 10 | 10 |
| 7 | 2-4 | 2 | 9 | 9 |
| 8 | 3-7 | 2 | 10 | 10 |
| 9 | 1-4 | 2 | 8 | 8 |

Example 2

A show and professional breeder of cattle has used transfer factor formulation with a cow herd of purebred Angus and Charolais, with unexpected and surprising results, using the following protocol.

Cows were given two ounces of the formulation of Table 3 at approximately Day 10 prior to breeding. At this time, a "seeder" (CIDR®, progesterone implant, available from Pfizer Animal Health) is placed intravaginally to synchronize estrus. At 72 hours prior to breeding, the CIDR was removed and follicular development was stimulated with an effective dose of LUTALYSE® (dinoprost tromethamine, available from Pfizer Animal Health). At this time, two ounces of the formulation of Table 3 was again given to the animal.

Use of the above protocol without administration of transfer factor formulation yielded about 75% conception on first breeding. Addition of the transfer factor formulation resulted in a rate of conception of about 98%.

Example 3

The breeder of Example 2 also tested transfer factor on donor cows. Without the use of transfer factor formulation, the best flush (donor) cow had averaged a yield of about 6 to 8 eggs; with usually only 1 or 2 eggs attaining Grade 1, the rest being Grade 2 and 3.

After administration to the cow of one ounce of the formulation of Table 3 at Days 5 and 6 prior to flushing, the number of fertilized eggs recovered was 12 eggs; 10 of these were Grade 1.

These surprising results are economically significant, as the most valuable cows may yield embryos that are valued at approximately $1000 each.

Example 4

Transfer factor formulation was administered to dairy cows post calving. One ounce of the formulation of Table 3 was administered on Monday and Friday, starting at 10 days after calving, until the cows came into heat for breeding. After implementation of this protocol, conception increased from about 30% to about 50%.

Example 5

Effect of Transfer Factor on Semen Production in Bull

A young bull nine months old was evaluated to have no live semen. The animal was then administered one ounce of the formulation of Table 3 daily for one month. After one month of the above protocol, 75 ampules of viable semen were collected from the animal, which is an above average yield.

Prior to transfer factor administration, the veterinarian who had examined the bull had advised waiting for a year to re-check the animal's semen quality. Without intending to be bound by any theory or theories of operation, it is believed that the unexpected results obtained suggest that administration of transfer factor formulation may stimulate spermatogenesis.

Example 6

Effects of Transfer Factor on Fertility in Sheep

The following demonstrates the effects of transfer factor on the fertility of sheep in a 35 to 40 ewe herd maintained for show stock.

No TF Protocols

In Year 1, an about 40% conception rate was achieved on first breeding, with a lamb crop of about 125% on 32 ewes. No TF product was used.

In Year 2, 32 ewes were bred, resulting in about 40% conception, with a lamb crop of about 140%.

In Year 3, 36 ewes were bred. These animals were treated with Aureomycin crumbles at 112.50 mg daily in their feed to combat the effect of stress. The rate of conception was about 40% over a 90 day period; the lambing crop was about 160%. No TF product was used.

TF Protocols

In Year 4, 43 ewes were bred. These animals were administered one ounce of the formulation of Table 3 in individual feed on each of Days 6 and 7 prior to breeding. LA 200 was administered to the ewes at a dosage of 9 mg per pound of body weight as an equivalent to aureomycin crumbles in the feed.

The bucks used to breed the ewes were administered one ounce of the formulation of Table 3 via drench on Days 29, 30, 13 and 14 prior to breeding.

Chelated sheep minerals were provided in feed to ewes and bucks.

Teaser bucks (who were either sterile or they had a breeding ring inserted in the back of the sphigmoid processes so they were unable extend their penises) were placed with ewes 15 days prior to breeding with "good" bucks.

41 of the 43 ewes conceived on the first breeding for a rate of about 95% conception. Lambing percentage was 85 lambs from 43 ewes, which is about a 198% lamb crop.

In Year 5, 43 ewes, treated as above, were bred with bucks also treated as above. Conception was completed in 20 days for 41 of the ewes. It is believed that the two ewes that did not conceive were too young and were thus pre-puberty.

Example 7

Thirty-five (35) mature Hampshire ewes in Santa Rosa with fertility difficulty demonstrated conception at about 40% for several years.

Administration of one ounce of the formulation of Table 3 on Days 6 and 7 prior to breeding increased conception to about 95%.

Example 8

Effects of Transfer Factor on Breeding of Swine

A study was conducted on a swine operation in Fordham County, South Dakota to test the efficacy of transfer factor. Prior to the study, conception normally averaged about 83 to about 88%, using sows bred after farrowing and newly bred gilts.

64 sows were administered 0.5 ounce/head/day of the formulation of Table 1 on Days 6 and 7 prior to breeding and again on two consecutive days 3 weeks prior to farrowing. Gilts were also administered 0.5 ounce/head/day of the formulation of Table 1 on Days 6 and 7 prior to breeding.

All sows, including controls (no TF formulation administered) and treated were challenged with a serious flu virus during pregnancy.

61 out of 64 treated sows conceived, for a conception rate of approximately 95.3%.

The data collected for the sows described above and their litters are summarized below in Table 5. DOA=Dead on Arrival Example 9

This study included 80 sows with second and third litters, 40 control and 40 treated.

Forty head received treatment consisting of 0.6 ounce of the formulation of Table 1 on Days 5 and 6 before breeding, and 0.6 ounce at Days 21 and 7 prior to farrowing (birthing).

The results were as follows:
A) Effect on fertility as measured by approximate rates of conception:
  Controls—90%
  Treated—95%
B) Death loss from birth through weaning at 17 days:
  Controls—12.7%
  Treated—2.7%
C) Weight gain thru weaning at 17 days:
  Approximately one half pound per head advantage for the treatment group.
D) Total weaned pigs:
  Controls—10.7 per litter
  Treated—11.2 per litter There were no inputs in this natural study, meaning no vaccines or antibiotics or hormones were administered to the animals.

Example 10

A 25-year old mare was diagnosed with granulosa cell tumor of the left ovary. The mare suffered from chronic abdominal pain; in addition, her blood tests for progesterone, testerone and inhibin indicated a high suspicion of a granulosa cell tumor. When initially diagnosed, the mare demonstrated a level of progesterone (0.1 ng/ml) consistent with an absence of active luteal tissue; a level of testosterone (64.8 pg/ml) that was marginally elevated for a non-pregnant mare; and an inhibin level (0.70 ng/ml) at the upper limit of normal for a non-pregnant mare.

After approximately nine (9) months of administration of the formulation of Table 2 at 141 grams daily, the ovary had shrunk about 80% and endocrine indices had returned to within normal limits. At this time, blood test results for progesterone (13.5 ng/ml) were consistent with active luteal tissue. Testosterone levels (27.7 pg/ml) were within normal limits for a non-pregnant mare. Inhibin levels (0.25 ng/ml) were likewise within normal limits for a non-pregnant mare.

Example 11

Effects of Transfer Factor on Yields of Fertilized Eggs from Blackbird Cows (Ovum Flush Study)

1) The first flush was performed with no TF product given. The animals were treated with effective dosages of Follicle Stimulating Hormone (FSH) (1 cc) and LUTALYSE® (1 cc) on days 7-6-5-4 to stimulate follicular development. The results were 18 non-fertile dead embryos.

TABLE 5

| | Number Born Alive | DOA | % DOA | Number Weaned | Average litter/sow | Avg. wean Weight (lbs.) | Days until weaning | Average Daily Gain (lbs.) |
|---|---|---|---|---|---|---|---|---|
| Control Sows (48) | 518 | 28 | 5.12 | 479 | 9.979 | 15.2 | 20.35 | 0.746 |
| Treated Sows (64) | 697 | 19 | 2.65 | 657 | 10.770 | 14.3 | 18.97 | 0.753 |

2) The second flush using the same protocol of FSH 1 cc and 1 cc LUTALYSE® on days 7-6-5-4 produced one (1) fertile egg.

3) Treatment with one ounce of the formula of Table 3 on days 7 and 6 with the same protocol as above (1 cc FSH and 1 cc LUTALYSE® day 7-6-5-4) resulted in eighteen (18) number one grade eggs and three (3) number 2 grade eggs.

In both treated animals and controls, LUTALYSE® was given on day 2 before flush am and pm (1 cc) with the flush done on day 1 in the morning.

Example 12

Effects of Transfer Factor on Bucking Bull Stock

This study contained two groups for recipient of fertilized eggs.

40 control cows received no TF product. 40 treated animals included mixed heifers and cows.
Serving Protocol:
40 cows and heifers were treated according to the following:

Day 1—CIDR® (synchronizing hormone placed in the vagina) in, administered two 0.5 ounce boluses of the formula of Table 3.

Day 2—administered two more boluses of the formula of Table 3.

Day 8—pulled the CIDR® and administered LUTALYSE® injection two cc and administered two boluses of the formula of Table 3.

Day of implantation of egg—two boluses of the formula of Table 3 were given at time of egg implanting.
Flush Cows Using the same protocol as above, two boluses were given with CIDR®, and when FSH was administered at 1 cc, two boluses were given day 7-6, but no administration on day 5-4, only FSH at 1 cc.
Results:

1) Flush cows were 15 in number. The numbers of eggs were increased from about 18 to 22%.

2) Recipient cows (cows the eggs are placed in for gestation) usually average about 50% conception, as measured by proof of pregnancy at 42 days.

In treated animals, conception increased to about 63% of the total of 40 treated cows and heifers; this represents an increase of about 13% in those who checked in calf at 42 days.

These data demonstrate effects of the administration of transfer factor formulations on tumors and on reproductive health.

It will be apparent to those skilled in the art that various modifications and variations can be made in the methods and compositions of the present inventions without departing from the spirit or scope of the invention. Thus, it is intended that the present invention cover the modification and variations of the inventions provided they come within the scope of the appended claims and their equivalents.

The terms and expressions which have been employed are used as terms of descriptions and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope on this invention.

In addition, where features or aspects of the invention are described in terms of Markush group or other grouping of alternatives, those skilled in the art will recognized that the invention is also thereby described in terms of any individual member or subgroup of members of the Markush group or other group.

Unless indicated to the contrary, all numerical ranges described herein include all combinations and subcombinations of ranges and specific integers encompassed therein. Such ranges are also within the scope of the described invention.

The disclosures of each patent, patent application and publication cited or described in this document are hereby incorporated herein by reference, in their entirety.

What is claimed is:

1. A method of increasing the quantity of Grade I embryos obtained from a female ruminant, comprising administering to the ruminant, five to seven days prior to the removal of embryos from the ruminant, an effective amount of a formulation comprising at least one encapsulated transfer factor selected from the group consisting of bovine colostrum transfer factor, avian transfer factor and a combination thereof, wherein the quantity of Grade I embryos obtained is greater than that obtained from a female ruminant who was not administered the formulation.

2. The method of claim 1, wherein the ruminant is selected from the group consisting of bovines, ovines and caprines.

3. The method of claim 1 wherein the production of ova in the ruminant is increased.

4. The method of claim 1 wherein the formulation further comprises at least one glucan.

5. The method of claim 4 wherein at least one glucan is present in at least one whole fungal organism.

6. The method of claim 5 wherein the concentration of at least one transfer factor in the formulation is between about 10 mg per oz and about 12,000 mg per oz and the concentration of at least one glucan is between about 10 mg of whole organism per oz and about 18,000 mg of whole organism per oz.

7. The method of claim 1 wherein at least one transfer factor is encapsulated with a hydrophobic or lipid coating that is between about 25 and about 150 wt % of the transfer factor.

8. The method of claim 1 wherein the bovine colostrum transfer factor is a fraction of colostrum comprising material that will pass through a nominal 10,000 Da filter.

9. The method of claim 1 wherein the formulation comprises powdered whole egg yolks comprising avian transfer factor.

10. The method of claim 1 wherein the formulation comprises bovine colostrum transfer factor and avian transfer factor.

* * * * *